United States Patent [19]

Kamei et al.

[11] Patent Number: 4,639,294

[45] Date of Patent: Jan. 27, 1987

[54] PROCESS FOR PRODUCTION SORBIC ACID

[75] Inventors: Noboru Kamei; Kinjiro Ikeda; Keishi Aoyama; Seitaro Hamano, all of Niigata, Japan

[73] Assignee: Daicel Chemical Industries, Ltd., Osaka, Japan

[21] Appl. No.: 755,518

[22] Filed: Jul. 16, 1985

[30] Foreign Application Priority Data

Jul. 16, 1984 [JP] Japan .............................. 59-146027

[51] Int. Cl.[4] .............................................. B01D 3/12
[52] U.S. Cl. ...................................... 203/88; 159/49; 203/89; 562/601
[58] Field of Search .................. 562/601, 600; 203/89, 203/72, 88; 159/5, 49

[56] References Cited

U.S. PATENT DOCUMENTS 3,960,939 6/1976 Sekiyama et al. .................... 562/601

Primary Examiner—Frank Sever

Attorney, Agent, or Firm—Sughrue, Mion, Zinn, Macpeak & Seas

[57] ABSTRACT

A process for producing sorbic acid is described, by first reacting crotonaldehyde with ketene to prepare a polyester, then decomposing the polyester with hydrochloric acid, separating the crude sorbic acid from the reaction solution, and purifying the separated sorbic acid, said purifying step comprising the following steps:

(a) continuously dissolving the crude sorbic acid in petroleum at a temperature in the range of from 100° to 140° C. while evaporating the residual water and hydrochloric acid from the solution of the sorbic acid in petroleum;

(b) separating the tar content from the petroleum solution in a separation column at a temperature in the range of from 100° to 140° C.; and (c) subjecting the mixture of sorbic acid and petroleum to flash evaporation in a film-type evaporator at a reduced pressure in the range of from 20 to 60 mmHg, with the evaporation residue being withdrawn from the bottom of the evaporator and recycled to step (a).

6 Claims, No Drawings

PROCESS FOR PRODUCTION SORBIC ACID

FIELD OF THE INVENTION

The present invention relates to an improved process for evaporative production of sorbic acid.

BACKGROUND OF THE INVENTION

Sorbic acid is currently produced by decomposing, either with hydrochloric acid, alkali, or heat, a polyester prepared by reacting crotonaldehyde with ketene. The method using hydrochloric acid involves no isomer production, and yields a product of the best quality with the highest efficiency. However, all of the conventional methods require a separate purifying step since the tar produced as a by-product during the reaction remains as an impurity together with the polyester residue. Even the relatively advantageous method using hydrochloric acid as a decomposing agent is not an exception, and the crude sorbic acid obtained by cooling and filtering the decomposed polyester is not entirely free from tar. The need for removal of the residual hydrochloric acid is an additional problem.

Conventionally, the crude sorbic acid is purified by treatment with activated carbon or by recrystallization from water or a mixture of water and an organic solvent. However, either of these techniques suffers from considerable disadvantages in economic terms resulting from the adsorption of the sorbic acid and its retention in the filtrate. Furthermore, the commercial operation of these methods requires complicated equipment.

The crude sorbic acid may be purified by distillation. However, sorbic acid is structurally liable to heat, and as soon as it is melted, it starts to polymerize, this tendency being increased as the sorbic acid becomes less pure. It is therefore almost impossible to sufficiently purify the crude sorbic acid by commercial distillation. Co-distillation techniques that claim to have solved this problem and which are superior to the other methods have been disclosed in German Pat. No. 1,044,803 and Japanese Patent Publication No. 4091/69. However, even these techniques are not completely satisfactory, for several reasons, such as the tendency of the sorbic acid to form a resin. The biggest problem is that hydrochloric acid remaining in the crude sorbic acid that has been decomposed with hydrochloric acid distills off with the sorbic acid in the subsequent distillation step and is carried into the crystals of purified sorbic acid.

SUMMARY OF THE INVENTION

The present inventors made various studies in order to overcome the problems of the above described conventional technique of co-distillation. As a result, the inventors have now succeeded in producing sorbic acid of improved quality by a simpler means of treatment, and this can be achieved in a higher yield with a lower capital cost.

Therefore, according to the present invention, there is provided a process for producing sorbic acid by first reacting crotonaldehyde with ketene to prepare a polyester, then decomposing the polyester with hydrochloric acid, separating the crude sorbic acid from the reaction solution, and purifying the separated sorbic acid, said purifying step comprising the following steps:

(a) continuously dissolving the crude sorbic acid in petroleum at a temperature in the range of from 100° to 140° C. while evaporating the residual water and hydrochloric acid from the solution of the sorbic acid in petroleum;

(b) separating the tar content from the petroleum solution at a temperature in the range of from 100° to 140° C.; and (c) subjecting the mixture of sorbic acid and petroleum to flash evaporation in a film-type evaporator at a reduced pressure in the range of from 20 to 60 mmHg, with the evaporation residue being withdrawn from the bottom of the evaporator and recycled to step (a).

Preferably, the process further comprises purifying a gas stream of the evaporated sorbic acid and petroleum by feeding (refluxing) an additional petroleum into the separation column from the top thereof, and condensing said gas stream by direct contact with a slurry of sorbic acid, petroleum, and water that is temperature-controlled by adiabatic cooling with the aid of water evaporation.

DETAILED DESCRIPTION OF THE INVENTION

The process of the present invention is hereunder described in more detail.

I. Dissolution in petroleum (and removal of hydrochloric acid)

It was first thought that the principal problems involved in the dissolution of crude sorbic acid in petroleum would be the corrosion of the vessel by the hydrochloric acid present in the sorbic acid, as well as the accelerated formation of a resin from the sorbic acid due to the hydrochloric acid or the metal dissolved into the solution as a result of corrosion. As it turned out, however, the actual problem in a batch system was the presence of from 200 to 300 ppm of residual hydrochloric acid in the sorbic acid.

The inventors conducted a series of experiments wherein the crude sorbic acid resulting from the decomposition of a polyester by hydrochloric acid was continuously dissolved in petroleum while performing the removal of water and hydrochloric acid from the solution. The results are summarized in Table 1.

TABLE 1

| Temperature (°C.) | 110 | 120 | 130 | 140 |
|---|---|---|---|---|
| Residual H$_2$O (%) | 0.15 | 0.015 | 0.010 | 0.005 |
| Residual HCl (ppm) | 700 | 20 | 10 | 5 |
| Total Residual Cl (%) | 0.08 | 0.07 | 0.07 | 0.07 |
| Degree of resin formation | low | low | moderate | high |

Note 1
Residence time: 2 hours
Other process conditions: Same as in Example 1, described hereinafter When the crude sorbic acid was continuously dissolved in petroleum at above 100° C., especially above 110° C., azeotropic distillation with petroleum enabled very effective removal of water and hydrochloric acid. However, sorbic acid has a tendency to polymerize while being in solution in petroleum, and is lost not only while the sorbic acid is dissolved in the petroleum, but also during the period when the solution is left to stand to allow separation of the insoluble tar content. The undesired polymerization of the sorbic acid could be suppressed to a significant degree by controlling the temperature of the solution below 140° C., especially below 130° C.

However, in spite of the temperature control, certain amounts of an orgaic chlorine containing compound remained in the solution (probably due to the binding of Cl with the tar).

The principal advantages of step I in the process of the present invention are such that the crude sorbic acid is continuously dissolved in petroleum while the temperature of the solution is controlled in order to suppress the polymerization of the sorbic cid and to eliminate completely the hydrochloric acid that may cause corrosion or deteriorate the sorbic acid product.

The petroleum that is used in the process of the present invention may be selected from among the fractions of any known lubricating oils that have boiling points of from 180° to 300° C. at atmospheric pressure. The petroleum is generally used in an amount of from 1 to 15 parts by weight, and preferably from 1 to 10 parts by weight, per part by weight of the crude sorbic acid.

The crude sorbic acid is dissolved in the petroleum at a temperature generally in the range of from 100° to 140° C., and preferably from 110° to 130° C., and desirable results may generally be obtained by continuing the dissolving step for from 1 to 4 hours.

II. Evaporation (and separation of tar)

The solution of the crude sorbic acid in petroleum contains an insoluble tar portion that must be removed. This tar content is like a hard coke and has no flowability, so, in the conventional methods, considerable difficulty has been encountered in withdrawing this tar continuously. Another serious problem has been that a significant amount of sorbic acid is lost in the concentrated residue left after evaporating the solution of sorbic acid in petroleum.

The concentrated residue has low viscosity and exhibits high solubility in petroleum, so the present inventors made various attempts to solve the above mentioned problem by recycling the residue to the step of dissolving the sorbic acid in the petroleum, and allowing the solution to stand for the purpose of tar removal. The results are summarized in Table 2.

TABLE 2

| Recycling | Yes | No |
|---|---|---|
| Degree of resin formation | Low | High |
| Homogenization/fluidization | Yes | No |

Note 2
Temperature: 130° C.
Other process condition: Same as in Example 1.

Aside from temperature effects, that were by no means insignificant, the concentrated residue was saturated in the solution of the crude sorbic acid in petroleum when the operation reached the stationary stage. At the same time, the insolubles in the residue mixed uniformly with the insoluble tar, and the resulting mixture could be separated from the solution by continuous withdrawal. The recycling of the residue caused no adverse effects in the evaporative concentration of the solution of sorbic acid in petroleum.

The principal advantages of step II are that the insoluble tar is homogenized and fluidized with the residue, permitting its separation from the petroleum solution by standing.

III. Evaporation (and recycling of the residue)

Other advantages resulting from the recycling of the residue are that the loss of sorbic acid into the residue is minimized, so as to reduce appreciably the content of sorbic acid in the separated tar, and that the polymerization reaction of the sorbic acid in the petroleum solution is suppressed, probably because the concentrated residue is saturated in the petroleum solution. Because of this great reduction in the loss of sorbic acid, the overall yield of the product sorbic acid is significantly improved.

In the process of the present invention, the solution of sorbic acid in petroleum is flash evaporated, e.g., with a film-type evaporator at a pressure of from 20 to 60 mmHg, and usually under heating at from 140° to 200° C. The concentrated residue forming as a result of evaporation is withdrawn for recycling in an amount that varies with the tar content in the solution of sorbic acid in petroleum, and the usual amount ranges from 10 to 30 parts by weight for 100 parts by weight of the initial charge. In actual operations, the amount of the residue withdrawn is controlled in terms of the temperature at the bottom of the evaporator.

The evaporated sorbic acid and petroleum are condensed and collected as a slurry. The collected condensate is optionally passed through an adsorbent such as activated carbon after dissolving with heating, and subsequently cooled to produce crystals of sorbic acid. Thereafter, the crystals may be treated by a conventional process consisting of centrifugation or filtering, and drying. If desired, another crystallization with water or a mixture of water and an organic solvent may be effected in order to obtain sorbic acid of a higher quality.

IV Evaporation (and supplying petroleum)

According to a preferred embodiment process of the present invention uses a refining (separation) column wherein an additional amount of petroleum is fed from the top instead of refluxing. The separation column may be of any conventional type that has a tier of perforated plates, and satisfactory results are obtained by using at least three perforated plates. The petroleum is fed preferably in an amount of from 0.2 to 1.0 part by weight per part by weight of the gas stream (mixed vapor).

Even the slightest amount of splash will impair the quality of the final product, so an especially highly efficient gas-liquid separation must take place in this step IV. If the operation period is extended, polymerized sorbic acid may cause scaling in the reactor (this makes it difficult to use a high efficiency packing-type separator).

V. Evaporation (and water quenching)

The solution of crude sorbic acid in petroleum contains from about 500 to 1,000 ppm of an organic Cl containing compound. It was therefore assumed that when this solution was subjected to evaporation, part of the organic Cl containing compound would be dissociated to form hydrogen chloride gas. In the subsequent step of condensing the mixed vapor of sorbic acid and petroleum, from 10 to 30% of the distilling hydrogen chloride gas would be carried into the crystals of sorbic acid. As a matter of fact, additional treatments such as cleaning of the crystal with water or a polar organic solvent are little effective in reducing the HCl level of the sorbic acid crystal.

The present inventors therefore made a series of experiments with a contact condenser through which a mixture of water and a slurry of the sorbic acid and petroleum was circulated for making contact with the stream of the gaseous mixture of sorbic acid and petroleum. The purposes of the experiments were to cool the gaseous stream by condensation upon contact with the stream of mixed gas and to cause the hydrogen chloride in said gaseous stream to be absorbed by the aqueous layer. The results are summarized in Table 3 below.

TABLE 3

| Water added (kg/hr) | 0 | 5 | 10 | 20 | 30 |
|---|---|---|---|---|---|
| HCl (ppm) in purified sorbic acid | 100–300 | 30–100 | 20–30 | 10–15 | ≦10 |

Note 3
The process operation was the same as in Example 1.

When the ratio of the additional water to sorbic acid was 0.5/1 and higher, and especially about 1/1, on a weight basis, the hydrochloric acid in the sorbic acid was effectively absorbed (extracted) by the aqueous layer and the purified sorbic acid contained very low levels of HCl.

A common surface condenser frequently suffers from scaling on the condensing surface, so, in the process of the present invention, a contact condenser is used for condensing the flow of a gaseous mixture of sorbic acid and petroleum. By using this particular type of condenser and circulating the mixture of water with a slurry of sorbic acid and petroleum, a sorbic acid product with a very low level of HCl can be recovered.

The initial composition of the slurry circulating in the process of the present invention may be approximately the same as that of the sum of the mixed vapor and supplementary water (e.g., 60% petroleum, 8% sorbic acid, and 32% water), and the subsequent composition is determined theoretically by material balances. The slurry is circulated in as large an amount as possible (e.g., about ten times the weight of the mixed vapor) to the extent that this will not adversely affect the heat balance in the condensing system. The supplementary water is added in an amount ranging from 2 to 10 times the weight of the distilled sorbic acid.

This preferred embodiment of the process of the present invention also has the advantage that the circulating slurry can be cooled adiabatically by the evaporation of water without using an external cooler. Water boils at 34° C. in a condensing system held at a pressure of 40 mmHg, so the slurry can be maintained at 34° C. by evaporating water without an external cooler. In order to attain this result, water needs to be evaporated in an amount at least half (theoretically one-fifth) the weight of the vapor mixture, and this requirement can be met by adding the supplementary water in an amount of 2 to 10 times the weight of the distilled sorbic acid.

When evaporation was performed under the conditions shown above, no deterioration of the sorbic acid occurred and the aqueous layer contained from 500 to 1,000 ppm of hydrochloric acid depending upon the amount of supplementary water added.

Troubles such as cavitation in the circulation pump and corrosion at the evaporator and condenser did not occur.

The slurry of sorbic acid, petroleum, and water emerging from the evaporator is centrifuged or filtered by a conventional method, and subsequently dried to produce snow white crystals of pure sorbic acid with low HCl levels.

The process of the present invention is hereunder described in further detail by reference to examples.

EXAMPLE 1

A glass vessel (capacity: 200 liters) equipped with a stirrer was continuously fed with 20 kg/hr of crude sorbic acid (20% water, 4% tar, 2,000–6,000 ppm of HCl) that was prepared by decomposition with HCl, and 64 kg/hr of a lubricating oil (b.p. range 200°–250° C.). After adding 20 kg/hr of the concentrated residue (described hereinafter), the dissolution of the sorbic acid in the lubricating oil and the removal of water and hydrochloric acid from the solution were performed at 120° C. The residence time was controlled at 2 hours. As a result, water was distilled at a rate of 4.0 kg/hr and the petroleum solution contained 0.015% of water and 20 ppm of HCl. Effective removal of water and HCl was thereby accomplished.

The solution was continuously fed to the separation step at a rate of 100 kg/hr. The residence time in the separation vessel (capacity: 200 liters) was 2 hours, and the setting tar layer was continuously withdrawn from the bottom of the vessel at a rate of 1 kg/hr. The tar separation and its continuous withdrawal could be performed smoothly by using the head difference and the operation was continued for several weeks without any trouble.

The upper layer in the solution was continuously fed to the evaporation step in an amount of 99 kg/hr. Evaporation was effected with a centrifugal film-type evaporator (heat transfer area: 1.0 m$^2$) at a pressure of from 50 to 60 mmHg while the jacket on the evaporator was heated with 9 kg/cm$^2$G of steam. A mixed vapor of sorbic acid and petroleum was obtained at a rate of 79 kg/hr. The concentrated residue having a temperature of 160° C. at the bottom of the evaporator was recovered at a rate of 20 kg/hr, and recycled continuously to the dissolving vessel. The recycled residue was highly flowable (viscosity: 500 cp at 150° C.).

The mixed vapor of sorbic acid and petroleum was passed through a mist separator and condensed by cooling so as to recover a mixed slurry of sorbic acid and petroleum. This slurry was cooled to 20° to 30° C., centrifuged and dried to obtain 15 kg/hr of sorbic acid. The supernatant obtained in the centrifugation step also contained 0.2 kg/hr of sorbic acid. The overall yield of sorbic acid was 94.9% in terms of the crude sorbic acid (dry basis) and 98.8% in terms of sorbic acid in the crude sorbic acid. The 1.2% loss in the latter case consisted of 0.2% sorbic acid in the tar withdrawn from the separation vessel and 1.0% sorbic acid that turned into resin.

One gram of the product sorbic acid was dissolved in 10 ml of methanol and the solution was found to have a color value of 95.0% by measuring the light transmission at 350 nm with a spectrophotometer. At the same time, another one gram of the sorbic acid was dissolved in 8.8 ml of aqueous 1N NaOH and the solution was found to have a color value of 97.5% by measuring the light transmission at 400 nm.

COMPARATIVE EXAMPLE 1

The same general treatment as in Example 1 was performed, except that the concentrated residue left in the evaporation step was discarded without being recycled to the dissolving vessel.

In a few hours, the withdrawal pipe in the separation vessel was plugged with tar, making subsequent continuous tar withdrawal impossible. The operation was discontinued and the inside of the vessel was cleaned. About 0.3 kg/hr of a solid tar had been deposited.

In order to increase the efficiency of concentrating (recovering) the evaporation residue, the jacket on the film evaporator was fed with 12 kg/cm²G of steam. This enabled the recovery of 1.3 kg/hr of a concentrated residue having a temperature of 170° C. at the bottom of the evaporator. This residue contained 20.1% of sorbic acid.

The total amount of the sorbic acid produced was 14.5 kg; the yield was 90.6% in terms of the crude sorbic acid, and 94.3% in terms of sorbic acid in the crude sorbic acid. The 5.7% loss in the latter case consisted of 1.7% sorbic acid in the residue and 4.0% sorbic acid that turned into a resin.

COMPARATIVE EXAMPLE 2

The procedure of Comparative Example 1 was repeated, except increasing the temperature in the dissolving and separating vessels to 140° C. Probably because the conversion of the sorbic acid into a resin was increased, the continuous operation was even more difficult to achieve, and the frequency of cleaning operations had to be increased.

In this Comparative Example, the concentrated residue having a temperature of 170° C. at the bottom of the evaporator was recovered at a rate of 3.6 kg/hr, and this residue contained 20.5% of sorbic acid. The total amount of the sorbic acid produced was 12.2 kg; the yield was 76.1% in terms of the crude sorbic acid and 79.2% in terms of sorbic acid in the crude sorbic acid. The 20.8% loss in the latter case consisted of 4.8% sorbic acid in the residue and 16.0% sorbic acid that turned into a resin.

EXAMPLE 2

A glass dissolving vessel (capacity: 200 liters) equipped with a stirrer was continuously fed with 20 kg/hr of crude sorbic acid (20% water, 4% tar on a dry basis, 4,000 ppm of HCl) that was prepared by decomposition with HCl and 64kg/hr of a commercial grade of lubricating oil (b.p. 200°–250° C.). The dissolution of the sorbic acid in the lubricant and the removal of water and HCl from the solution were effected at 120° C., with a residence time of 2 hours. Four kilograms of water were distilled per hour, and the solution contained 0.015% of water and 20 ppm of HCl (inorganic Cl containing compound). The total Cl content as measured by the combustion method was 700 ppm.

The solution of sorbic acid in lubricant was continuously fed to the evaporation step in an amount of 79.8 kg/hr. Evaporation was effected with a centrifugal film-type evaporator (heat transfer area: 1.0 m²) at a pressure of 50 to 60 mmHg while steam was supplied into the jacket at a rate of 12 kg/cm²G. The evaporating flow of the gaseous mixture of sorbic acid and lubricant was passed through a separation column having four perforated plates while the lubricant was fed from the top of the column in an amount of 50 kg/hr.

A mixed vapor of sorbic acid and lubricant came off the top of the column in an amount of 129 kg/hr whereas a concentrated residue was recovered from the bottom of the evaporator (170° C.) in an amount of 1.3 kg/hr. The total Cl level in the residue was 2.3% and the sorbic acid content was 20.1%.

The vapor mixture of sorbic acid and lubricant was condensed by cooling with a contact condenser through which a mixture of water with a slurry of sorbic acid and lubricant having the same composition as that of the mixed vapor feed had been circulated. The feed was recovered in the form of a slurry of sorbic acid, lubricant and water. The circulating slurry was cooled adiabatically by the evaporation of supplementary water added into the system at a rate of 75 kg/hr. The condensation system had a temperature of 34° to 36° C. and a pressure of about 40 mmHg. The recovered slurry was centrifuged and dried to obtain 14.0 kg/hr of sorbic acid.

The filtrate of the centrifuged product contained 0.5 kg/hr of sorbic acid, and the total yield of sorbic acid was 94.3% in terms of sorbic acid. One gram of the sorbic acid obtained was dissolved in 10 ml of methanol and the solution was found to have a color value of 96% by measuring the light transmittance at 350 nm with a spectrophotometer. At the same time, another one gram of the sorbic acid was dissolved in 8.8 ml of aqueous 1N NaOH and the solution was found to have a color value of 98.5% by measuring the light transmittance at 400 nm. The product sorbic acid contained not more than 10 ppm of hydrochloric acid.

EXAMPLE 3

The same treatment as in Example 2 was followed, except that the concentrated residue obtained in the evaporation step was recycled to the dissolving vessel. Sorbic acid was produced in an amount of 14.9 kg/hr, and the total yield of sorbic acid including the one present in the filtrate was 99.4% in terms of sorbic acid.

A solution of the product sorbic acid in methanol had a color value of 96% whereas a solution in aqueous 1N NaOH had a color value of 98.5%. During the process operation, the total Cl level as well as the tar content of the solution in lubricant increased, but the sorbic acid as the final product never contained more than 10 ppm of HCl.

While the invention has been described in detail and with reference to specific embodiments thereof, it will be apparent to one skilled in the art that various changes and modifications can be made therein without departing from the spirit and scope thereof.

What is claimed is:

1. A process for producing sorbic acid by first reacting crotonaldehyde with ketene to prepare a polyester, then decomposing the polyester with hydrochloric acid, separating the crude sorbic acid from the reaction solution, and purifying the separated sorbic acid, said purifying step comprising the following steps:
   (a) continuously dissolving the crude sorbic acid in petroleum at a temperature in the range of from 100° to 140° C. while evaporating the residual water and hydrochloric acid from the solution of the sorbic acid in petroleum;
   (b) separating the tar content from the petroleum solution at a temperature in the range of from 100° to 140° C.;
   (c) thereafter substantially precluding the formation of solid state (rigid) tar by subjecting the mixture of sorbic acid and petroleum to flash evaporation in a film-type evaporator at a reduced pressure in the range of from 20 to 60 mmHg,; and
   (d) recycling residue from the bottom of the evaporator to step (b).

2. A process for producing sorbic acid as in claim 1, further comprising purifying a gas stream of the evaporated sorbic acid and petroleum by feeding (refluxing) additional petroleum into the separation column from the top thereof, and condensing said gas stream by direct contact with a slurry of sorbic acid, petroleum, and water that is temperature-controlled by adiabatic cooling with the aid of water evaporation.

3. A process for producing sorbic acid as in claim 2, wherein the additional petroleum for purifying the gas stream of the evaporated sorbic acid is fed into the separation column from the top thereof in an amount of from 0.2 to 1.0 part by weight per part by weight of the gas stream.

4. A process for producing sorbic acid as in claim 1, wherein the petroleum is used in an amount of from 1 to 10 parts by weight per part by weight of the crude sorbic acid.

5. A process for producing sorbic acid as in claim 3, wherein the crude sorbic acid is dissolved in the petroleum at a temperature of from 110° to 130° C.

6. A process for producing sorbic acid as in claim 1, wherein the flash evaporation is conducted at a temperature of from 140° to 200° C.

* * * * *